United States Patent [19]
Crooker et al.

[11] Patent Number: 5,169,995
[45] Date of Patent: Dec. 8, 1992

[54] INHIBITED 14LB

[75] Inventors: Richard M. Crooker, Lehigh; James P. Lavelle, Abington Township, Montgomery County; Maher Y. Elsheikh, Tredyffrin, all of Pa.

[73] Assignee: Elf Atochem North America, Inc., Philadelphia, Pa.

[21] Appl. No.: 773,480

[22] Filed: Oct. 9, 1991

[51] Int. Cl.$^5$ .................. C07C 17/42; C07C 19/02
[52] U.S. Cl. .................. 570/111; 252/182.2; 252/182.24; 570/102; 570/116; 570/119; 570/122
[58] Field of Search ............... 570/111, 122, 116, 102, 570/119

[56] References Cited

U.S. PATENT DOCUMENTS 2,364,588 12/1944 Morris et al. .................. 570/116
4,948,474 8/1990 Brooks et al. .................. 204/158.21
4,950,816 8/1990 Tung et al. .................. 570/179

FOREIGN PATENT DOCUMENTS 1-056630 3/1989 Japan .................. 570/116
1-056631 3/1989 Japan .................. 570/116
1-268650 10/1989 Japan .................. 570/110
2-204424 8/1990 Japan .................. 570/110

OTHER PUBLICATIONS

R. M. Crooker et al., "Accelerated Aging Study of HCFC 14lb in Polyurethane Premix," J. Cellular Plastics, 1989, 25(6), pp. 609–617.

Primary Examiner—Joseph E. Evans

[57] ABSTRACT

Storage-stable compositions of 14lb which are inhibited against decomposition with additives such as alpha-methylstyrene.

13 Claims, No Drawings

INHIBITED 141B

FIELD OF THE INVENTION

This invention relates to novel compositions containing 1,1-dichloro-1-fluoroethane ("141b") and inhibitors such as alpha-methylstyrene, more particularly to compositions of 141b which are stabilized against decomposition during storage.

BACKGROUND OF THE INVENTION

Much attention has been focused on 141b in recent years as a replacement for CFC-11 (trichlorofluoromethane) as a foam blowing agent, as a solvent, and so forth. In the manufacture of 141b, however, such as by the reaction of hydrogen fluoride with 1,1,1-trichloroethane or vinylidene chloride ("VDC"), unwanted impurities such as unsaturated carbon compounds (including VDC) have been found to result. Thus, processes have been developed for purifying 141b via photochlorination and/or activated carbon treatments, such as disclosed in U.S. Pat. Nos. 4,948,479 and 4,950,816.

It has now been found, however, that with or without such purification procedures 141b is unstable in storage, resulting in the formation of such unwanted by-products as phosgene. Thus, the industry is in need of storage-stable, inhibited 141b formulations.

SUMMARY OF THE INVENTION

A storage-stable composition is provided containing 141b and an effective amount of an inhibitor selected from alpha-methylstyrene ("AMS"), diethylhydroxylamine ("DEHA"), 1,2-hexadecene oxide ("HDO"), beta-pinene oxide ("BPO"), alpha-pinene oxide ("APO"), 1,2-epoxybutane ("EB"), alpha-glycidyl isopropyl ether ("GIE"), triphenyl phosphite ("TPP"), 4-benzyloxyphenol ("BOP"), and 1, 2,3-trihydroxybenzene ("THB").

DETAILED DESCRIPTION OF THE INVENTION

It has now been found that 141b is stabilized against decomposition during storage by the addition of an inhibitor selected from the ten compounds named above, preferably AMS, DEHA, HDO, BPO, or APO.

The inhibitor can be in amounts as low as about 0.005 weight %, based on the weight of the 141b, more typically in amounts from about 0.02 to about 2%, preferably 0.05 to 1%.

When intended for use as a blowing agent, these storage-stable compositions may also be incorporated in a foam premix and include an organic polyol or a fully formulated (B-side) premix formulation containing polyol, catalyst, surfactant, and, optionally, other additives. Typical polyols are, for example, Stepanol PS 2502A, an aromatic polyester polyol sold by the Stepan Company; Terate 203, an aromatic polyester polyol sold by Hercules, Inc.; Pluracol Polyol 975, a sucrose-based polyol sold by BASF; Poly-G 71-530, a polyether polyol sold by Olin; and Quadrol, an amine-based polyol supplied by BASF. Typical catalysts include Potassium HEX-CEM, a potassium octoate sold by Mooney Chemicals; Polycat 41, N,N,N-tri(dimethylaminopropyl)cyclohexatriazine catalyst sold by Air Products; Polycat 8, an N,N-dimethylcyclohexylamine catalyst sold by Air Products; Dabco TMR-30, a 2,4,6-tri(dimethylaminomethyl)phenol supplied by Air Products; and Dabco K-15, a potassium 2-ethylhexoate in diethylene glycol supplied by Air Products. A typical surfactant is Dow Corning 193, a silicone polymer surfactant.

The invention was illustrated in the following examples using a "pure" 141b made by a process such as taught in U.S. Pat. No. 4,948,479, i.e., by reacting hydrogen fluoride and 1,1,1-trichloroethane, photochlorinating, and distilling. Typical product analyses are given in Table 1 of that patent. The invention is, however, equally applicable to 141b made by other processes, such as by reacting HF with vinylidene chloride. While "purified" material is used for the purpose of illustration, the inhibitors are considered to be effective in stabilizing 141b regardless of whether or not the crude reaction product has been purified with photochlorination, activated carbon, or other treatments.

In each of the examples glass bottles were filled with inhibitor (if any) and 141b, the bottles were capped, air was admitted to the bottles up to 30 psig; the bottles were placed in a box so as to form a ring about a 450 watt mercury argon lamp also located in the box; the bottles were then irradiated and phosgene levels were determined by a colorimetric test using nitrobenzylpyridine reagent and comparing the results against a standardization curve. In Example 1 a "purified" 141b was used in which phosgene had already formed upon storage to see if the invention inhibitors could arrest further phosgene formation—in fact, in most cases they reduced the phosgene levels. In Examples 2 and 3 fresh, purified 141b was used in which phosgene had not yet formed to any detectable level. UV radiation is used in the tests since several hours of UV radiation have been found to simulate several weeks of thermal aging studies.

EXAMPLE 1

Five Hours UV Radiation

| Inhibitor (0.5 weight %) | Phosgene Levels (in ppm) At Start and After UV | |
|---|---|---|
| AMS | 13 | 12 |
| APO | 10 | 3 |
| HDO | 10 | 6 |
| BPO | 12 | 2 |
| EB | 11 | 8 |
| GIE | 10 | 8 |
| TPP | 10 | 10 |
| BOP | 12 | 9 |
| THB | 12 | 6 |

EXAMPLE 2

Fifteen Hour UV Radiation

| Inhibitor (0.5 weight %) | Phosgene (ppm) After UV |
|---|---|
| None | 6.5 |
| DEHA | <0.5 |
| HDO | <0.5 |
| BPO | <0.5 |

EXAMPLE 3

Eighteen Hour UV Radiation

| Inhibitor (in weight %) | Phosgene (ppm) After UV |
|---|---|
| None | 36.0 |
| 0.3 AMS | 0.25 |
| 0.1 AMS | 0.53 |

-continued

| Inhibitor (in weight %) | Phosgene (ppm) After UV |
|---|---|
| 0.053 AMS | 0.42 |
| 0.021 AMS | 0.42 |
| 0.0053 AMS | 1.6 |
| 0.3 APO | 0.46 |
| 0.1 APO | (bottle broke) |
| 0.053 APO | 0.28 |
| 0.021 APO | 0.82 |
| 0.0053 APO | 1.4 |

What is claimed is:

1. A composition stable against the formation of phosgene during storage consisting of 1,1-dicholoro-1-fluoroethane and an effective amount of an inhibitor selected from alpha-methylstyrene, diethylhydorxylamine, 1,2-hexadecene oxide, beta-pinene oxide, alpha-pinene oxide, 1,2-epoxybutane, alpha-glycidyl isopropyl ether, triphenyl phosphite, 4-benzyloxyphenol, and 1,2,3-trihydroxybenzene.

2. A composition as in claim 1 wherein the inhibitor is alpha-methylstyrene.

3. A composition as in claim 1 wherein the inhibitor is diethylhydroxylamine.

4. A composition as in claim 1 wherein the inhibitor is 1,2-hexadecene oxide.

5. A composition as in claim 1 wherein the inhibitor is beta-pinene oxide.

6. A composition as in claim 1 wherein the inhibitor is alpha-pinene oxide.

7. A composition stable against the formation of phosgene during storage comprising 1,1-dichloro-1-fluoroethane and an effective amount of diethylhydorxylamine.

8. A method of stabilizing 1,1-dichloro-1-fluoroethane against the formation of phosgene which consists of the addition thereto of an effective amount of an inhibitor selected from alpha-methylstyrene, diethylhydroxylamine, 1,2-hexadecene oxide, beta-pinene oxide, alpha-pinene oxide, 1,2-epoxybutane, alpha-glycidyl isopropyl ether, triphenyl phosphite, 4-benzyloxyphenol, and 1,2,3-trihydroxybenzene.

9. A method as in claim 8 wherein the inhibitor is alpha-methylstyrene.

10. A method as in claim 8 wherein the inhibitor is diethylhydroxyamine.

11. A method as in claim 8 wherein the inhibitor is 1,2-hexadecene oxide.

12. A method as in claim 8 wherein the inhibitor is beta-pinene oxide.

13. A method as in claim 8 wherein the inhibitor is alpha-pinene oxide.

* * * * *